(12) United States Patent
Carpenter et al.

(10) Patent No.: US 7,521,252 B2
(45) Date of Patent: Apr. 21, 2009

(54) METHODS FOR FORMING PALLADIUM ALLOY THIN FILMS AND OPTICAL HYDROGEN SENSORS EMPLOYING PALLADIUM ALLOY THIN FILMS

(75) Inventors: Michael A. Carpenter, Scotia, NY (US); Zhouying Zhao, Schenectady, NY (US)

(73) Assignee: The Research Foundation of State University of New York, Albany, NY (US)

( * ) Notice: Subject to any disclaimer, the term of this patent is extended or adjusted under 35 U.S.C. 154(b) by 822 days.

(21) Appl. No.: 11/049,833

(22) Filed: Feb. 3, 2005

(65) Prior Publication Data

US 2005/0169807 A1 Aug. 4, 2005

Related U.S. Application Data

(60) Provisional application No. 60/541,613, filed on Feb. 4, 2004.

(51) Int. Cl.
*G01N 33/00* (2006.01)
*C22F 1/14* (2006.01)

(52) U.S. Cl. ............ 436/144; 148/678; 422/90; 422/91; 356/437

(58) Field of Classification Search ............ 422/90–91; 205/775; 436/144; 148/678; 356/437
See application file for complete search history.

(56) References Cited

U.S. PATENT DOCUMENTS

| 5,670,115 | A * | 9/1997 | Cheng et al. ............ 422/90 |
| 6,006,582 | A | 12/1999 | Bhandari et al. ............ 73/23.2 |
| 6,539,774 | B1 | 4/2003 | Zinck et al. ............ 73/23.2 |
| 6,569,490 | B2 | 5/2003 | Yadav et al. ............ 427/58 |
| 6,596,236 | B2 | 7/2003 | DiMeo, Jr. et al. ............ 422/88 |
| 2002/0017126 | A1 | 2/2002 | DiMeo, Jr. et al. ......... 73/31.05 |
| 2002/0154310 | A1 | 10/2002 | DiMeo, Jr. et al. .......... 356/437 |

(Continued)

FOREIGN PATENT DOCUMENTS

JP 60159632 A 8/1985 .............. 250/474.1

(Continued)

OTHER PUBLICATIONS

Hughes, et al., "Thin-film palladium and silver alloys and layers for metal-insulator-semiconductor sensors," J. Appl. Phys. vol. 62, No. 3; Aug. 1, 1987, pp. 1074-1083.

(Continued)

*Primary Examiner*—Lyle A Alexander
*Assistant Examiner*—Dennis M White
(74) *Attorney, Agent, or Firm*—Heslin Rothenberg Farley & Mesiti P.C.

(57) ABSTRACT

Methods for forming hydrogen sensing materials include forming a palladium alloy thin film having less than about 83 atomic percent of palladium, and annealing the palladium alloy thin film to relieve residual stress and increase atomic intermixing of the nanorystaline lattice, while maintaining a grain size close to the grain size of the nonannealed palladium alloy thin film. For example, the sensing material may include a palladium-gold alloy thin film having about 60 atomic percent of palladium and about 40 atomic percent of gold. The palladium-gold alloy thin film is then annealed at a temperature of about 200 degrees Celsius for 1 hour. Methods for detecting hydrogen containing gas in which the hydrogen sensing material is maintained in a single phase when exposed to the hydrogen containing gas, and optical hydrogen sensors are also disclosed.

12 Claims, 10 Drawing Sheets

U.S. PATENT DOCUMENTS

| | | | |
|---|---|---|---|
| 2002/0171839 A1 | 11/2002 | DiMeo, Jr. et al. | 356/437 |
| 2003/0056570 A1 | 3/2003 | Shin et al. | 73/25.05 |
| 2003/0057109 A1 | 3/2003 | Wang et al. | 205/775 |
| 2003/0079999 A1 | 5/2003 | Penner et al. | 205/775 |

OTHER PUBLICATIONS

Jayaraman, RaviPrakash; "Thin Film Hydrogen Sensors: A Materials Processing Approach"; Pennsylvania State University, College of Engineering, Graduate School Thesis, Dec. 2002; pp. 1-112.

Xomeritakis, George and Lin, Y.S.; "Fabrication of thin metallic membranes by MOCVD and sputtering"; Journal of Membrane Science; 2 vol. 133, No. 2, 1997; pp. 217-230.

Hughes, R.C. and Schubert, W.K.; "Thin films of Pd/Ni alloys for detection of high hydrogen concentrations"; J. Appl. Phys. 71(1), Jan. 1, 1992; pp. 542-544.

Hughes, R.C., et al.; "Solid-State Hydrogen Sensors Using Palladium-Nickel Alloys: Effect of Alloy Composition on Sensor Response"; J. Electrochem.Soc., vol. 142, No. 1, Jan. 1995; pp. 249-254.

Thomas, Ross C. and Hughes, Robert C.; "Sensors for Detecting Molecular Hydrogen Based on Pd Metal Alloys"; J. Electrochem. Soc. vol. 144, No. 9, Sep. 1997; pp. 3245-3249.

Yaniv, Dr. Zvi; "Nanotechnology Sensor Can Help Predict Electrical Transformer Failure"; Practicing Oil Analysis Magazine; Nov. 2003.

\* cited by examiner

Fig. 25

METHODS FOR FORMING PALLADIUM ALLOY THIN FILMS AND OPTICAL HYDROGEN SENSORS EMPLOYING PALLADIUM ALLOY THIN FILMS

PRIORITY INFORMATION

This application claims priority from pending U.S. Provisional Application No. 60/541,613, filed on Feb. 4, 2004, entitled "Compositional Control Of Palladium Alloy Thin Films: Optimization Of Nanoscale Films For Hydrogen Sensor", the entire subject matter of which is incorporated herein by reference.

FIELD OF THE INVENTION

This invention relates generally to hydrogen sensors, and more specifically to methods for forming palladium alloy thin films for use in optical hydrogen sensors.

BACKGROUND OF THE INVENTION

The demand for hydrogen as a next generation, clean and renewable energy source has stimulated considerable efforts towards developing sensitive, reliable, and cost effective hydrogen sensors for the fast detection of hydrogen leaks below the lower explosive limit (LEL) of 4.65% by volume ratio of hydrogen to air. Currently, palladium (Pd) or Pd alloys (less than 10 percent metal such as silver or nickel) are commonly used as the sensing material, due to the high sensitivity and selectivity of palladium to hydrogen.

Upon exposure to hydrogen, the Pd and Pd alloy (less than 10 percent metal) absorb hydrogen and form palladium hydride (PdH), a process which can be monitored via the change in reflectance/transmittance or electrical conductivity of the Pd or Pd alloy (less than 10 percent metal). A limiting factor in the fast detection of hydrogen leaks is the intrinsic α to β PdH phase transition that pure Pd or Pd alloy (less than 10 percent metal) undergoes upon exposure to hydrogen concentrations near and below the lower explosive limit (LEL), typically ranging between 0.1% and 2%. For example, response times as long as 3,600 seconds have been observed for optical based palladium hydrogen sensors. Such slow response times at these hydrogen concentrations are characteristic of critical slowing down phenomena that occur at the phase transition of the material. See Kalli et al., K. Kalli, A. Othonos, C. Christofides, $J.\ Appl.\ Phys.$ 91, 3829 (2002) and Zhao et al., Anal. Chem. 76, 6321 (2004). In addition, cyclic loading and unloading of hydrogen will also cause mechanical problems like blistering or delamination of the palladium films from substrates leading to poor sensor durability.

An attempt has been made with the addition of silver (Ag) to palladium in the gate metal of metal-insulator-semiconductor gas sensing diodes to improve the performance and change the selectivity of the sensors for a variety of reactions. Diodes with between 10% and 45% silver have been shown to respond to hydrogen gas. For low hydrogen level testing (250-ppm or 0.025% $H_2$), Ag content of over 40% gave poor performance, as well as 15% and 21% alloys. 10% and lower Ag showed faster response than pure Pd. 32% showed a fast initial response with a slow approach to steady state. See, Hughes, et al., "Thin-film palladium and silver alloys and layers for metal-insulator-semiconductor sensors", $J.\ Appl.\ Phys.$ 62 (3), pages 1074-1083, 1 Aug. 1987.

There is a need for further development of hydrogen sensors, and more specifically, to methods for forming palladium alloy thin films such as for use in all-optical based hydrogen sensors with proven reliability and a seconds level response time.

SUMMARY OF THE INVENTION

In a first aspect, the present invention provides a method for forming a hydrogen sensing material which includes forming a palladium-gold alloy thin film comprising about 60 atomic percent of palladium and about 40 atomic percent of gold, and annealing the palladium-gold alloy thin film at a temperature of about 200 degrees Celsius to about 300 degrees Celsius.

In a second aspect, the present invention provides a method for forming a hydrogen sensing material which includes forming a palladium alloy thin film comprising less than about 70 atomic percent of palladium and greater than about 30 atomic percent of a metal, and annealing the palladium alloy thin film to relieve residual stress and increase the Pd/metal intermixing in the nanocrystalline lattice, while maintaining a grain size close to the grain size of the nonannealed palladium alloy thin film.

In a third aspect, the present invention provides a method for detecting hydrogen containing gas which includes providing a hydrogen sensing material as noted above, projecting light onto the hydrogen sensing material, exposing the hydrogen sensing material to the hydrogen containing gas, maintaining the hydrogen sensing material in a single phase when exposing the hydrogen sensing material to the hydrogen containing gas, and observing a change in light transmitted through or reflected from the hydrogen sensing material due to exposure to the hydrogen containing gas.

In a fourth aspect, the present invention provides an optical hydrogen sensor which includes a hydrogen sensing material as noted above, a light source for projecting light onto said hydrogen sensing material, and a light detector for detecting at least one of light transmitted through and reflected from said hydrogen sensing material.

In a fifth aspect, the present invention provides a hydrogen sensing material which includes a palladium-gold alloy thin film having about 60 atomic percent of palladium and about 40 atomic percent of gold, and wherein the palladium-gold alloy thin film is generally stress free with a generally homogeneous nanocrystalline material composition.

In a sixth aspect, the present invention provides a hydrogen sensing material which includes a palladium-gold alloy thin film comprising less than about 83 atomic percent of palladium and greater than about 17 atomic percent of a metal, and wherein the palladium-gold alloy thin film is generally stress free with a generally homogeneous nanocrystalline material composition

BRIEF DESCRIPTION OF THE DRAWINGS

The subject matter which is regarded as the invention is particularly pointed out and distinctly claimed in the concluding portion of the specification. The invention, however, may best be understood by reference to the following detailed description of various embodiments and the accompanying drawings in which:

DETAILED DESCRIPTION

The present invention is directed to hydrogen sensors such as for the detection of leaks in hydrogen infrastructures such as in the implementation of hydrogen as the next generation of clean and renewable energy sources, detection of hydrogen as a reagent in industrial processing environments, detection of hydrogen gas as a by-product in industrial processing environments or the buildup of hydrogen gas in a chemical reaction, and detection of hydrogen gas in automobile and other transportation applications. In particular, the present invention is directed to methods for forming hydrogen sensing materials that do not undergo a phase transition. More particularly, the hydrogen sensing materials are thermally treated for signal enhancement and grain size control for enhanced signal change and fast time response characteristics while exhibiting buffering properties for enhanced reliability. These formed materials can be utilized as the sensing element in both optical and electrical based sensors.

In addition, the present invention is directed to optical hydrogen sensors with a seconds scale response time and reliability providing advantages over conventional electrical-based hydrogen sensors. These advantages include utilization for remote sensing applications, environments with electromagnetic interferences or sensing applications with a large background hydrocarbon concentration which would interfere with sensors based on heated catalytically active materials. Furthermore, the optical hydrogen sensor design is intrinsically safe as the active sensing material does not require an electric circuit in contact with the hydrogen environment.

Figure 1:
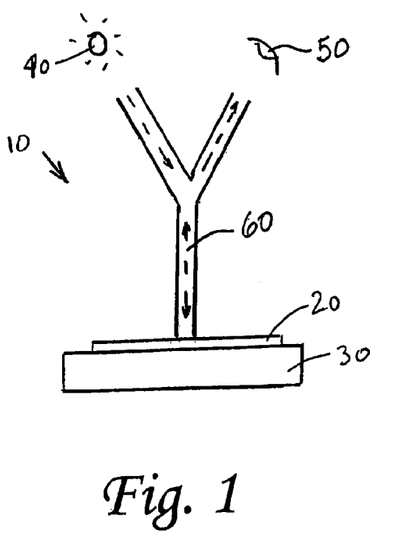
FIG. 1 is one embodiment of a reflective optical hydrogen sensor having a thin film hydrogen sensing material in accordance with the present invention.

FIG. 1 illustrates one embodiment of a reflective optical hydrogen sensor 10 having a thin film hydrogen sensor material 20 in accordance with the present invention disposed on a substrate 30, a light source 40, a light detector 50, and an optical fiber 60. The bifurcated optical fiber 60 directs light from light source 40 to the surface of thin film hydrogen sensing material 20, and receives and transmits reflected light from the surface of thin film hydrogen sensing material 20 to detector 50. The substrate may comprise a glass substrate for supporting the thin film hydrogen sensing material.

Figure 2:
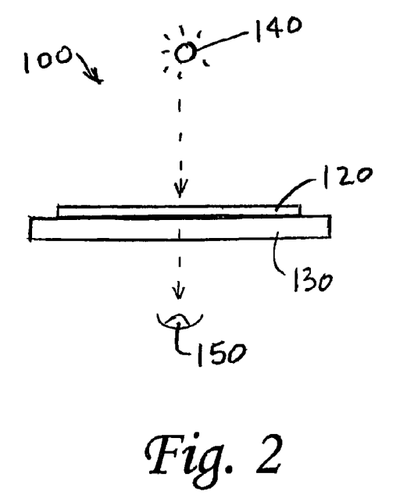
FIG. 2 is one embodiment of a transmission optical hydrogen sensor having a thin film hydrogen sensing material in accordance with the present invention.

FIG. 2 illustrates one embodiment of a transmission optical hydrogen sensor 100 having a thin film sensing material 120 in accordance with the present invention disposed on a substrate 130, a light source 140 disposed above thin film sensing material 120, and a light detector 150 disposed below thin film sensing material 120. Light from light source 140 is directed toward a top surface of thin film sensing material 120, transmitted through the thickness of thin film sensing material 120, and the transmitted light form the bottom surface of the thin film sensing material 120 is then detected by detector 150. The substrate may comprise a glass substrate for supporting the thin film hydrogen sensing material.

When the devices of FIGS. 1 and 2 are used for the detection of hydrogen containing gas, as the thin film hydrogen sensing material absorbs hydrogen, the thin film hydrogen sensing material allows less light from the light source to be reflected or more light to be transmitted through the thin film hydrogen sensing material.

As described in greater detail below, the technique of the present invention includes the use of thin film palladium alloys with the alloying element in large enough concentrations such that the PdH $\alpha$ to $\beta$ phase transition is inhibited during the detection of hydrogen gas. Since the phase transition does not occur in these materials when used as a hydrogen sensing material for the detection of hydrogen, the critical slowing down phenomena is inhibited.

As described in greater detail below, the technique of the present invention includes the use of thin film palladium alloys with the alloying element in large enough concentrations such that the PdH $\alpha$ to $\beta$ phase transition is inhibited upon exposure to hydrogen during the detection of the hydrogen gas. Since the phase transition does not occur in these materials when used as a hydrogen sensing material for the detection of hydrogen, the critical slowing down phenomena is inhibited.

The use of palladium alloys with alloying contents greater than the minimum amount required to prevent the α to β phase transition also provides the benefit of providing intrinsic buffering characteristics between the palladium alloy thin film and the substrate thus enhancing the long term reliability of the sensing material. Likewise with this intrinsic buffering capacity there is no need for an additional film deposited between the substrate and the thin film to alleviate the stress which would otherwise occur during hydrogen uptake. The utilization of nanoscale thin films also enhances the time response of the sensing device.

A thermal annealing pretreatment step significantly enhances the signal change of the sensing materials. Desirably, the annealing pretreatment is selected so that the thin film does not undergo or experiences little grain growth. This allows using a palladium alloy film where the palladium component is below 70% and having a 10 nanometer or less grain size which allows for a fast time response. The subsequent use of the sensing material at operating temperatures below the annealing temperature does not induce further grain growth which would lead to long term degradation in the sensing properties (both signal change and response time). Furthermore, since the PdH phase transition is dependent on the alloy composition, one can tune the alloy composition to avoid the phase transition, and in doing so optimize the resulting signal change (signal change increases with Pd content) and response time for the range of targeted hydrogen concentrations within a particular sensing environment.

The present invention may include hydrogen sensors with faster response and recovery times (5 seconds and below at 4% $H_2$) than that of existing pure palladium and high content palladium alloy (about 90% palladium) over a hydrogen concentration range from 0.045% to 50% thus allowing for hydrogen leak detection capabilities with enhanced safety benefits. Another advantage is enhanced reliability and stability due to the intrinsic buffering characteristics, stemming from the use of a palladium alloy with alloying content greater than 30%, along with a thermal pretreatment with grain size growth suppression.

Test Station

Figure 3:
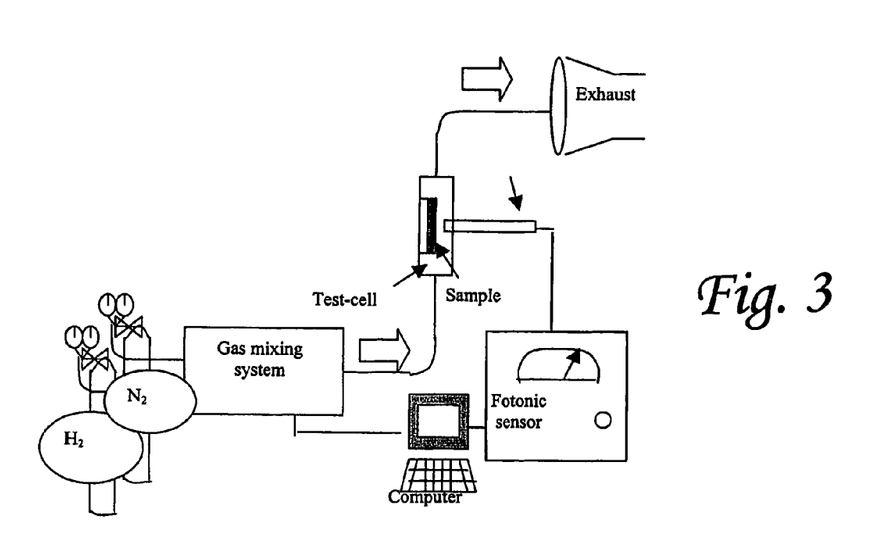
FIG. 3 is a diagrammatic illustration of a reflection based test station.

FIG. 3 illustrates a schematic diagram of a testing station. The palladium alloy thin films as described below, were mounted in a 20 cubic centimeter stainless steel chamber.

The response characteristics of the palladium alloy thin films, as discussed below, were measured by an intensity modulation-based fiber optic sensor, MTI 1000 Fotonics Sensor, which utilizes a bifurcated optical fiber bundle to direct a white light source to the thin films and collect the reflected light for detection using a silicon-photodiode. In order to prevent measured signal drift, the Fotonics system used a control feedback circuit for a constant white light power source.

First Sample Preparation and Hydrogen Sensing Tests

In a first embodiment of the present invention, a 20 nanometer thick film of palladium (60% in at. %) and gold (40% in at. %) was deposited on an acetone pre-cleaned glass substrates (about 0.5 inch×0.5 inch) by DC magnetron sputtering of the alloy target (of the same composition) at constant current of 40 mA and 75 mTorr Ar pressure.

Two sets of these Pd (60 at. %) and Au (40 at. %) samples were initially investigated. The first set, included an as-deposited thin film (denoted $A_0$) with no annealing, and a deposited thin film annealed at 200° C. (denoted $A_{200}$). A second set, contained an as-deposited thin film and those annealed at temperatures of 100° C., 150° C., 200° C., 250° C., 300° C., 350° C., and 400° C., respectively, (denoted $B_0$, $B_{100}$, $B_{150}$, $B_{200}$, $B_{250}$, $B_{300}$, $B_{350}$, and $B_{400}$). All the annealing treatments were done in 760 Torr of Ar flowing at 1200 sccm for one hour.

Figure 4:
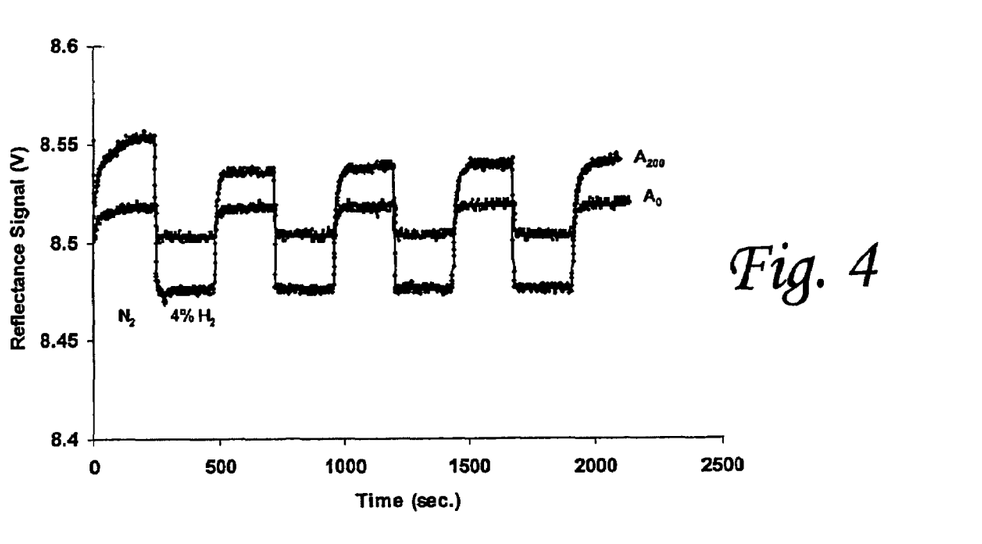
FIG. 4 is a graph of the reflectance signal over time for a first palladium alloy thin film without annealing, and a second 200° C. annealed palladium thin film in accordance with the present invention.

FIG. 4 illustrates the optical reflectance responses of the as-deposited ($A_0$) and 200° C. annealed ($A_{200}$) thin films to exposure of 4% $H_2$ in $N_2$. The total test gas flow, pressure and temperature were maintained at 1200 sccm, 760 Torr, and about 25° C., respectively.

An optical reflectance change of about 15 mV (or a 0.18% relative change) was observed for the as-deposited thin film, $A_0$. The annealing treatment resulted in a factor of four increase in signal change with a nearly unchanged response time of 5 seconds for the 200° C. annealed film ($A_{200}$). The as-deposited film, $A_0$, did not show a measurable signal change for $H_2$ concentrations below about 1% (not shown in FIG. 4). While the thermally annealed films, $A_{200}$, became sensitive to 0.05% or 500 ppm of hydrogen gas ($H_2$), as described below. The films present a fast and reversible hydrogen response due to the annealing process and suppression of the palladium hydride phase transition.

In the second set of samples, the Pd/Au thin films, as described above, were annealed at temperatures ranging from 100° C. to 400° C., in 50° C. increments.

Figure 5:
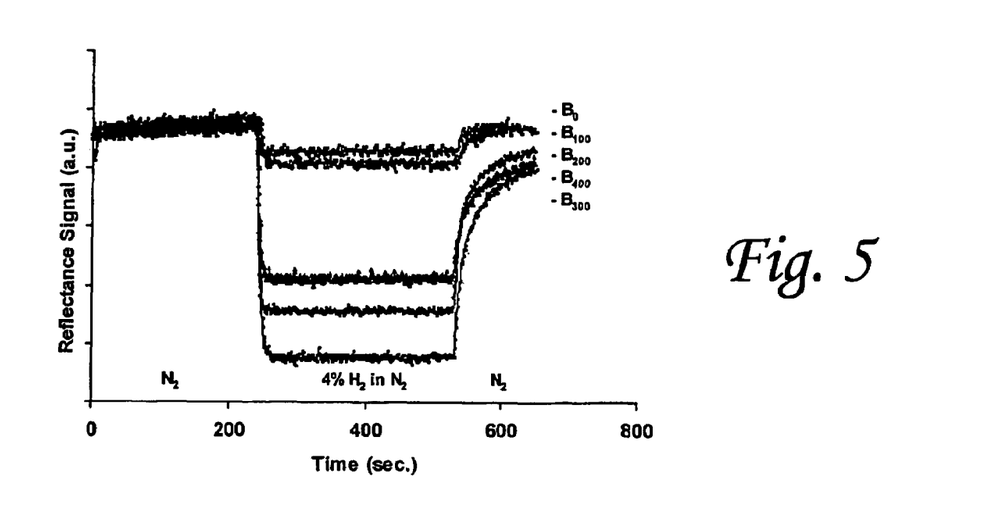
FIG. 5 is a graph of the reflectance signal over time for a nonannealed palladium alloy thin film and a plurality of palladium alloy thin films annealed at different temperatures in accordance with the present invention.

FIG. 5 illustrates the resultant reflectance response curves for a single cycle exposure of 4% $H_2$ in $N_2$ for the annealed samples, with the curves being shown in steps of 100° C. increments. As seen in FIG. 5, annealing at a temperature of 100° C. for sample $B_{100}$ provides no significant improvement on the signal change relative to that of the as-deposited film $B_0$.

However, there is a step-like increase (a factor of more than six, as compared to the as-deposited sample) in the signal change for the 200° C. annealed sample $B_{200}$ and a further increase to a maximum for $B_{300}$, and then a decrease for $B_{400}$.

Figure 6:
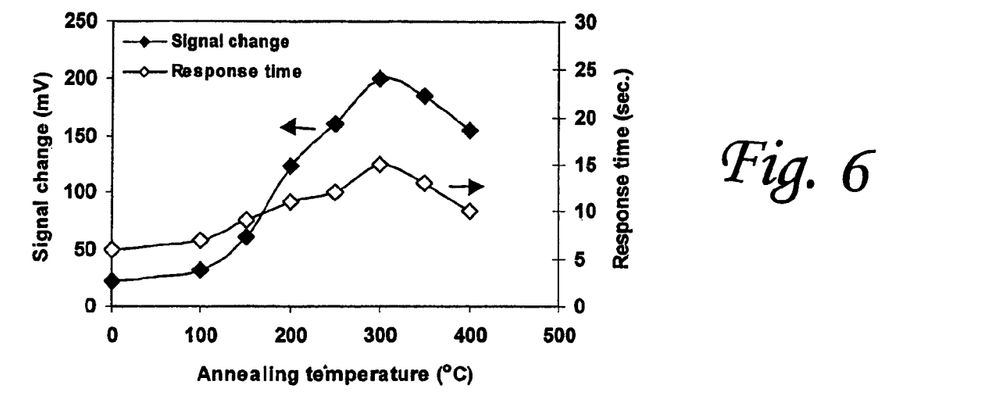
FIG. 6 are graphs of the reflective signal change and response time for the palladium alloy thin films of FIG. 5 with respect to the annealing temperature.

As shown in FIG. 6, the trends in signal change and response time are more apparent where the signal change and response times are plotted for sample set B with respect to the annealing temperature. The response time for a full signal change slightly increases with the annealing temperature and peaks at about 14 seconds for $B_{300}$. As a trade off between a large signal change and a short response time, annealing at about 200° C. appears to be an optimal annealing temperature for these thin films.

Grain Size

Since the thermal annealing pretreatment changes the corresponding microstructure of the Pd/Au thin films, an XRD (X-ray diffraction) study was performed to examine the microstructure dependence on the annealing temperature and its correlation with the resulting hydrogen absorption characteristics.

XRD patterns of the as-deposited films and thermally annealed films were collected on a Scintag XDS 2000 X-ray diffractometer using $CuK_\alpha$ (1.54 Å) radiation. A scan step of 0.02° and accumulation count time of 50 seconds were selected to yield a good signal to noise ratio for the 20 nanometer thin films. The peak position and full width at half maximum (FWHM) was determined, after a background subtraction and a Modified-Lorentz function peak-fitting procedure, to within the specified tool resolution of 0.02°. The peak width of the fiber textured Pd/Au (111) was performed with Stock correction using the corresponding peak of a fully annealed film for calculation of the average nanocrystalline grain size from the Scherrer equation, $d=0.941\ \lambda/B\ \cos(\theta)$, where d is the interspacing of the diffraction planes, $\lambda$ is the x-ray wavelength, B is the FWHM and $\theta$ is the Bragg angle. The obtained grain size was in agreement with those obtained through TEM image analysis.

Figure 7:
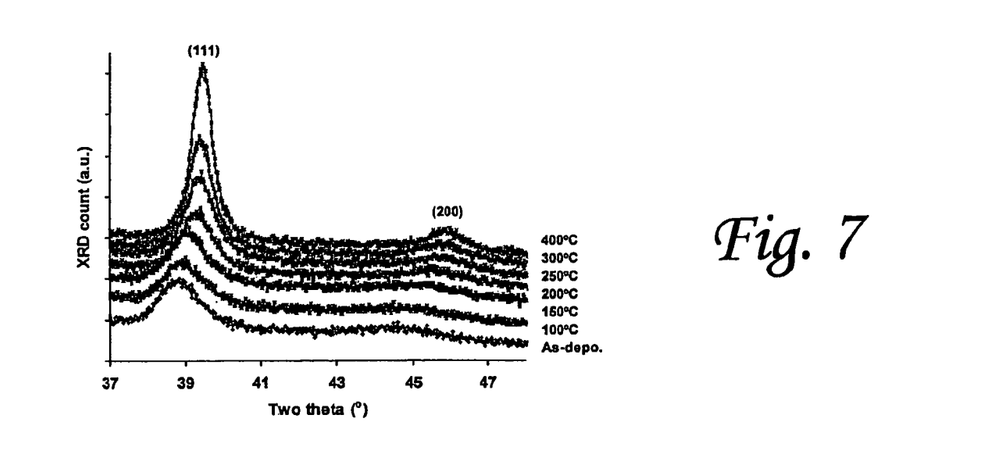
FIG. 7 is a graph of the x-ray diffraction patterns of the palladium alloy thin films of FIG. 5.

The Pd/Au alloy thin films possess (111) texture, similar to other metals. FIG. 7 compares the normal $\theta$-$2\theta$ scan XRD patterns for the non-annealed sample $B_0$ and those annealed at temperatures from 100° C. to 400° C. ($B_{100}$-$B_{400}$). The Pd/Au (111) peak narrows by approximately 50% and shifts by 0.6° from $B_0$ to $B_{400}$ with the increase in annealing temperature.

Figure 8:
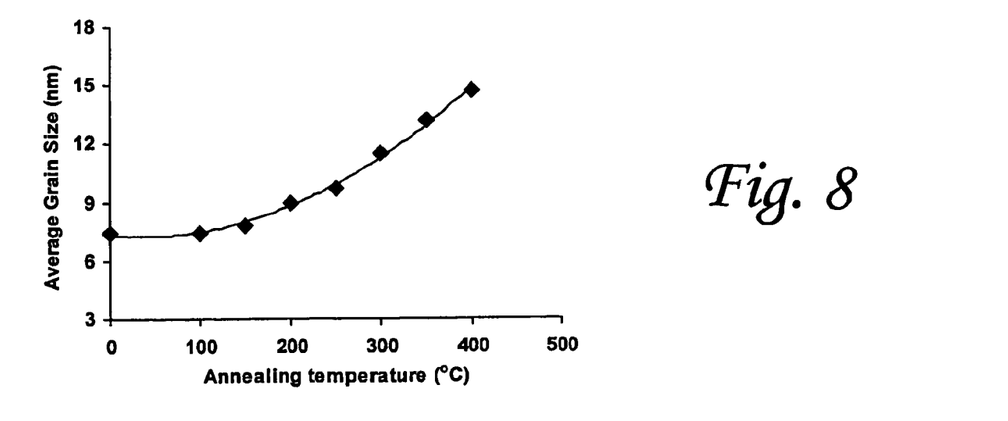
FIG. 8 is a graph of the grain size of the plurality of palladium alloy thin films of FIG. 5 with respect to the annealing temperature.

From the FWHM of the XRD peaks, the average grain size as a function of the annealing temperature was obtained and plotted in FIG. 8. As shown in FIG. 8, the grain size is about 7 nanometers for $B_0$ and remains nearly unchanged for $B_{100}$ and then undergoes a steady growth to about 15 nanometers for $B_{400}$. It is established that XRD resolved grains are mostly defect-free coherent diffraction domains surrounded by disordered grain boundaries, while the number of atoms in the coordination shells of nanocrystallites is substantially lower than in course-grained lattices. An increase in the average size of a diffraction domain due to a reduction in the disordered grain boundary increases the available Pd/Au lattice sites. Considering that the nature of hydrogen (H) absorption into the Pd/Au films is via the occupation of atomic H into the octahedral interstitials of the Pd fcc crystal lattice, it is believed that the observed grain growth is one of the factors causing the increased H absorption for the films annealed up to 300° C., which results in the increase in the optical signal change as shown in FIG. 6.

Although the presence of a large number of grain boundaries in nanocrystalline Pd has been considered to be the reason for the larger H solubility observed in α phase Pd hydride, the H solubility in β phase Pd hydride is lower compared to that in course-grained Pd, and tends to decrease with a decrease in Pd grain size, due to a reduction of the available Pd lattice sites. This size-dependence is assumed to be valid for Pd alloys. According to the material p-c phase diagram, the investigated Pd and Au (40%) film is associated with only β phase Pd hydride, thus, its H solubility ought to be increasing with the grain growth or grain boundary reduction, as discussed above. The subsequent decrease (FIG. 6) in signal change for the films annealed at the higher temperatures ($B_{350}$ and $B_{400}$) was initiated by a thermal-mechanical deterioration, which will be discussed below.

It is worth noting that the average grain size is as large as 15 nanometers for $B_{400}$ after the heat treatment at 400° C. with a significant agglomeration. The nanocrystalline state will be ideal for sensors for fast response kinetics, thus constraining the grain size with as little aggregation as possible by using a proper annealing temperature.

Internal Stress Relaxation

The Pd/Au (111) peak position of the as-deposited film $B_0$ is centered at 38.8° as shown in FIG. 7, which is about 0.6° lower than the peak position of $B_{400}$. The $B_{400}$ sample displays a nearly identical peak position to that of a theoretically stress-free film with the nominal composition of the Pd/Au sputtering target (60/40). The low-angle shift in the XRD peak position for the as-deposited sample reflects about 1.3% relative change of the d-spacing in the films normal direction, and should be attributed to both internal stress and composition of the nanocrystalline alloy grains within the film. A quantitative XRD analysis allows for the simultaneous determination of the stress and composition for the sample set B with the results presented in FIG. 9 and FIG. 11.

Figure 9:
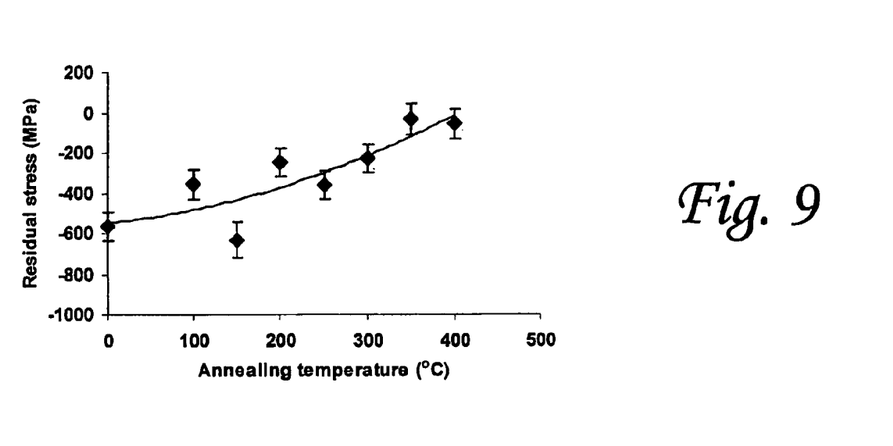
FIG. 9 is a graph of the residual stress of the plurality of palladium alloy thin films of FIG. 5 with respect to the annealing temperature.
Figure 10:
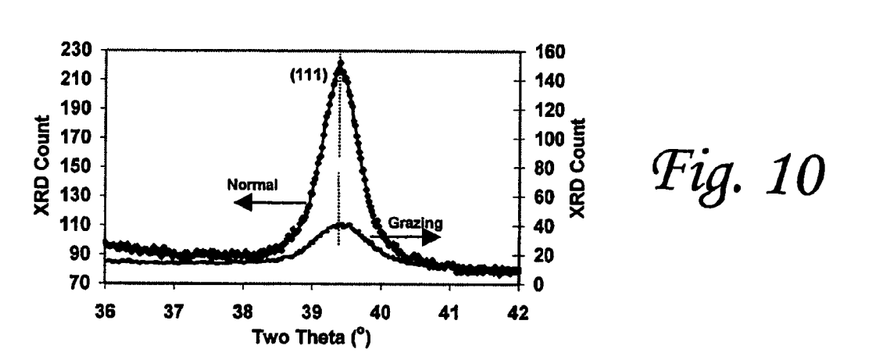
FIG. 10 is a comparison of XRD (111) Pd/Au peaks collected in normal and grazing incident angles for the 400° C. annealed sample.

As observed in FIG. 9, the as-deposited Pd/Au film $B_0$ is under a compressive stress of about 560 MPa, which is within typical values and of the same stress state reported for a variety of nanoscaled thin films. The stress within the annealed films is progressively reduced to nearly zero for the 400° C. annealed sample $B_{400}$, with the resultant microstructure almost fully relaxed. For this film, the XRD (111) Pd/Au peaks collected from normal and grazing incident angles are located at almost the same $2\theta$ position as shown in FIG. 10, consistent with the stress free state in the film. The stress relaxation occurred simultaneously with the steady grain growth in the films as shown in FIG. 8, illustrating a close correlation between the stress and grain growth as described below.

The compressive stress is partially originated from the argon (Ar) gas trapped in the films during the plasma deposition process, which is supported by the blistering revealed in the SEM images taken of the annealed films, as discussed below. The second contribution is believed to arise from an intrinsic volume stress component balanced by interface forces at grain boundary areas to achieve mechanical equilibrium. The interface force becomes non-negligible in nanoscaled thin films because of its reverse order dependence on the characteristic length scale of microstructures, i.e., the grain size. Consequently, there is also believed to be a higher pressure in the grains than the surroundings prescribed by the interface forces. This may explain the wide observations of compressive stresses (tens to a hundreds of MPa) in a variety of nanostructured thin films, regardless of the material preparation methods employed. Consistent with the data in FIGS. 8 and 9, compressive stress is reduced with a reduction in the grain boundaries.

It has been observed that there is a dependence between grain-size and the thermodynamics of palladium and palladium alloys. Compared to bulk or coarse grained materials, the nanophase films have narrowed miscibility gaps, downshifted and tilted pressure plateaus, and lowered critical temperatures. It has been speculated that the higher pressure in the nanocrystallites, resulting from the increase in interface forces is a root cause for the above characteristics. Specifically, a higher compressive stress or pressure within the grains is thought to induce an increased downshift of the pressure plateau, leading to a reduced total H solubility. Therefore, it is reasonable to assume that the H absorption or solubility increase observed for the films annealed up to 300° C. (FIG. 6), is also a direct result of the corresponding reduction of internal compressive stress from the as-deposited film.

Nanocrystallite Composition Evolution

Figure 11:
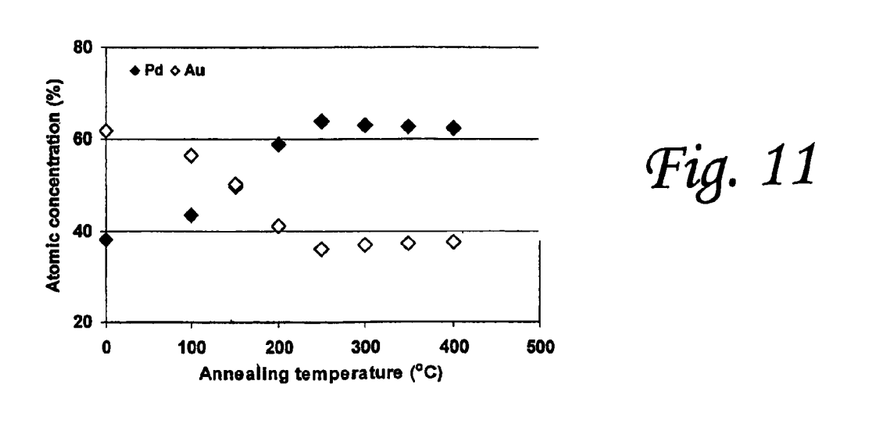
FIG. 11 is a graph of the atomic concentration of the nanocrystalline grains, determined through analysis of the XRD data displayed in FIG. 7, of the plurality of palladium alloy thin films of FIG. 5 with respect to the annealing temperature.
Figure 12:
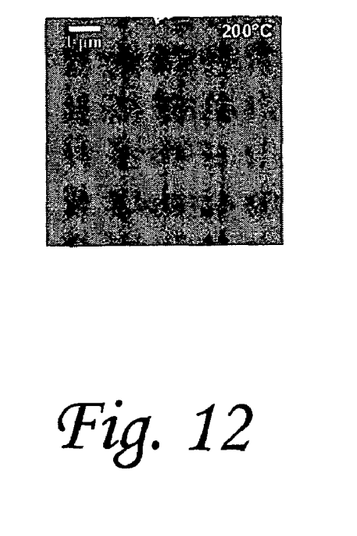
FIG. 12-15 are scanning electron microscopy images (having the same scale) of the annealed palladium alloy thin films at temperatures of 200° C., 300° C., 350° C., and 400° C., respectively.
Figure 13:
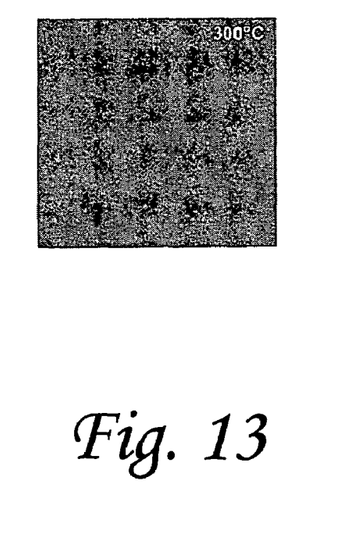
Figure 14:
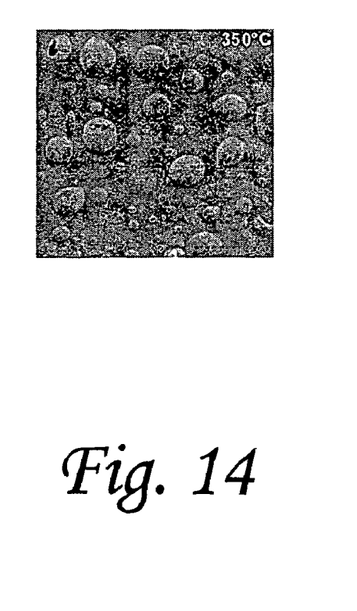
Figure 15:
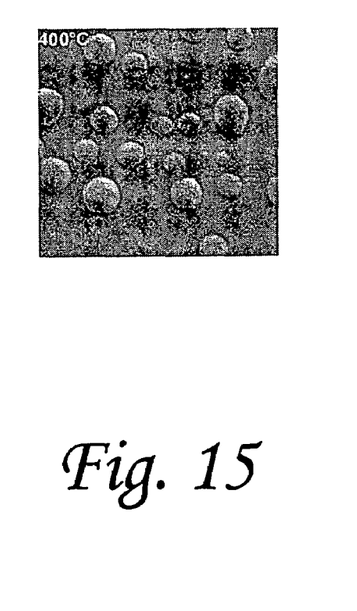

FIG. 11 illustrates the variation of the XRD composition for the as-deposited and the annealed Pd/Au nanocrystalline thin films. It is surprising that the XRD derived Pd:Au ratio of the as-deposited film is only about 40:60, opposite to the nominal composition (60:40) of the sputtering target. This is an indication of palladium reduction in the nanocrystalline grains of the as-deposited film, with Pd enrichment in a non-alloyed and disordered form in the grain boundary area and thus invisible to XRD detection. The XRD composition experienced a step-like change with heat treatment only after the temperature was elevated to 200° C. (for $B_{200}$), and for the films annealed at temperatures above 250° C. the compositions were in good agreement, within 3 at %, with the nominal composition of the sputtering target.

Such a palladium reduction in the nanocrystallites of the sputter deposited thin films was unexpected, however this result is strongly supported by several recent findings with chemical solution synthesized Pd/Au nanoparticles pointing out that silica supported Pd/Au particles have an atomic ratio of (40:60) instead of the predicted value based on the metal loading (82:18) used in the synthetic process, and concluding the material to contain far more gold rich alloy particles, which were surrounded by a highly dispersed palladium rich portion. See, Nakagawa et al.; Takashi Nakagawa, Hiroaki Nitani, Shuji Tanabe, Kenji Okitsu, Satoshi Seino, Yoshiteru Mizukoshi and Takao A. Yamamoto, Ultrasonics Sonochemistry, Vol. 12, 249 (2005). The fundamental controlling mechanism is not very clear, but is thought to be related to the faster nucleation and growth rate of gold compared to that of palladium, irrespective to the specific material synthetic methods utilized. Accordingly, it is understandable that the as-deposited films, $A_0$ and $B_0$ have a low H absorption since a large potion of palladium is not within the crystalline lattice sites.

The as-deposited microstructure has an unchanged and low hydrogen absorption capability at room temperature as evidenced by the unchanged H absorption even after multiple cycles of $H_2$ exposure (FIG. 1). The heat treatment promoted the atomic intermixing or alloying, and as a result, with Pd incorporation into the crystalline lattice, the XRD determined composition approaches the nominal composition via a step-like change beginning at an annealing temperature of about 200° C., the same temperature the Au/Pd structure begins to change into a random alloy (see Nakagawa reference cited above). The intermixing completed in the films annealed at temperatures above 250° C. with their consequent XRD compositions leveling off at the nominal composition. The data suggest that the atomic intermixing requires an activation step, at roughly 200° C. for the investigated Pd/Au films. The step-like composition change correlates well with the observed sharp enhancement of the H absorption as shown in FIG. 6, illustrating a consistent behavior.

Surface Morphology Variation (SEM Analysis)

According to the previous discussion, the signal changes from the Pd/Au films annealed at temperatures above 300° C. ($B_{350}$ to $B_{400}$) is expected to continuously increase with their grain growth (FIG. 8) or at least remain unchanged following the stress release (FIG. 9) and composition stabilization (FIG. 11), rather than slightly decrease as shown in FIG. 6. A visual inspection of samples $B_{350}$ and $B_{400}$ showed that the films were dull and less reflective in appearance.

A further inspection of the surface properties of the annealed films using scanning electron microscopy (SEM), revealed a significant change in their surface morphologies, as shown in FIGS. 12-15. From the exhibited images, one can see a large quantity of minor blisters appearing on sample $B_{300}$ and micron diameter blisters forming on samples $B_{350}$ to $B_{400}$ (while no blisters were observed with films annealed at temperatures above 500° C., which is not shown). Similar blistering effects have been observed and extensively studied for a variety of hydrogen and deuterium ion irradiated materials. The blistering has been found to arise from the ion implantation induced hydrogen or deuterium gas absorption and segregation into high pressure bubbles. The blistering strongly depends on process temperatures, such as a post-irradiation annealing temperature. It is believed that for the thin films of the present invention, blistering stems from the annealing temperature dependent segregation of pre-adsorbed gases on the glass substrate surface and in particular the working gas trapped by plasma ion bombardment in the sputtering deposition process. The trapped working gas is often used to explain the reason for the observed compressive stresses in sputtering-deposited films.

The large size blisters on the films increased the surface roughness and optical scattering, which caused a reduction in the observed signal change for these high temperature annealed films, $B_{350}$ to $B_{400}$, (FIG. 6), thus impeding the detection of actual H absorption in these films. The decreased response times may result from the blister induced surface area increase and loose structure within the films, which accelerated the gas response rate for $B_{350}$ and $B_{400}$. The observed mechanical deterioration suggests the importance for choosing an optimal annealing temperature, e.g., 200° C., for the Pd/Au thin films discussed above.

Conclusion Regarding the First Samples

The sputter deposited 20 nanometer thick films show a small reflectance signal change at even 4% $H_2$ concentration, while displaying a promising fast response time (about 5 seconds) owing to suppression of Pd hydride phase transition. The as-deposited films, consisting of about 7 nanometers nanocrystalline grains with a high number of grain boundaries, has been found to have a compressive stress of about 560MPa, and an unexpected low Pd content (about 40%) in the grains relative to the overall thin film Pd concentration (60%), with Pd enrichment in the disordered grain boundary. The low H absorption characteristics of the as-deposited films can be altered by a post-deposition annealing of the thin film at a moderate temperature, 200° C., for a four to six times increase in signal change while the thin film still retains a 5 second response time. The annealing process also cures the microstructure allowing for subsequent sensing stability, reliability and durability. Annealing at temperatures above 300° C. leads to mechanical deterioration (blistering), and thus, a reduction in signal change due to the blister induced optical scattering. The mechanism for H absorption enhancement is attributed to the annealing promoted microstructure variation: grain growth, stress reduction or release and atomic intermixing of Pd from its enrichment and disordered state at the grain boundary into the Pd/Au grain lattice. A post-deposition annealing treatment also proves to be an efficient method to stimulate or activate H absorption in other nanocrystalline Pd alloys.

Second Sample Preparation and Hydrogen Sensing Test

In a second embodiment of the present invention, 20 nanometer thick alloy films of Pd and Au (40% at. %) were sputter deposited on glass substrates, with resulting nanocrystallites of about 7 to 8 nanometers in size measured by x-ray diffraction. The thin films were then annealed at 200° C. in an argon atmosphere for one hour. After annealing, each film was cured. The curing process consisted of two consecutive cycles of 4% hydrogen exposure for 10 minutes followed by exposure to pure nitrogen for 20 minutes at room temperature. After deposition and after each of the hydrogen exposure tests, the films were stored in a clear plastic storage container under ambient conditions. No special storage measures were taken for these films as this more closely mimics field deployed ambient exposure conditions.

Figure 16:
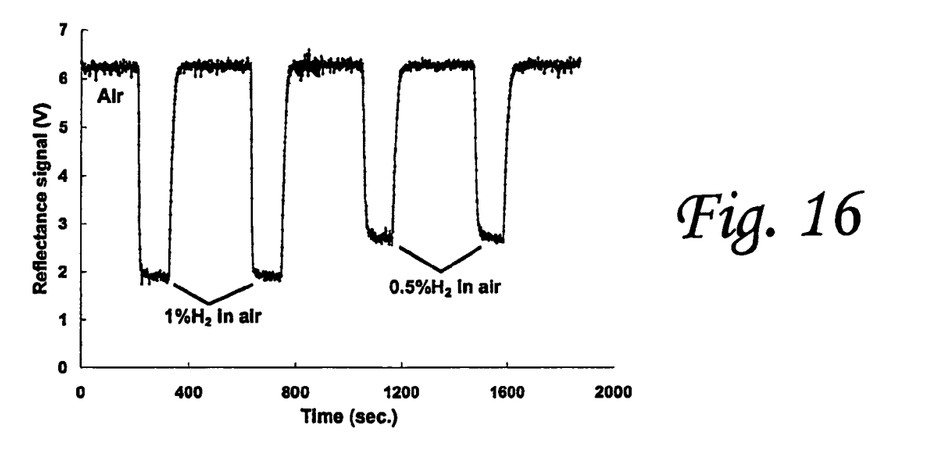
FIG. 16 is a graph of the reflectance signal over time for another 200° C. annealed palladium alloy thin film for two separate pairs of exposure cycles, one at 1% hydrogen gas in air, and the other at 0.5% hydrogen gas in air.

Using the test station shown in FIG. 3, the reflectance response of the Pd and Au (40% at. %) alloy film for two separate pairs of exposure cycles at an operating temperature of 40° C., the first going from air to 1% hydrogen in air, and the second going from air to 0.5% hydrogen in air, was observed and is illustrated in FIG. 16. The total test gas flow and pressure were maintained at 1,200 sccm and 760 Torr, respectively. After each test, the chamber was opened to air to aid the recovery of the sample reflectance signal to the initial reflectance levels.

As observed in FIG. 16, a response time for a full signal change is only 8 seconds and 15 seconds at 1% and 0.5% hydrogen concentrations, respectively, while the recovery time was measured to be 20 seconds for both gas exposures. Response and recovery times are defined as the time required to achieve 100% of the corresponding signal change for the adsorption and desorption of hydrogen. The results repeat very well and the fast response time at these hydrogen concentrations are attributed to the suppression of the α to β phase transition in the thin film.

Figure 17:
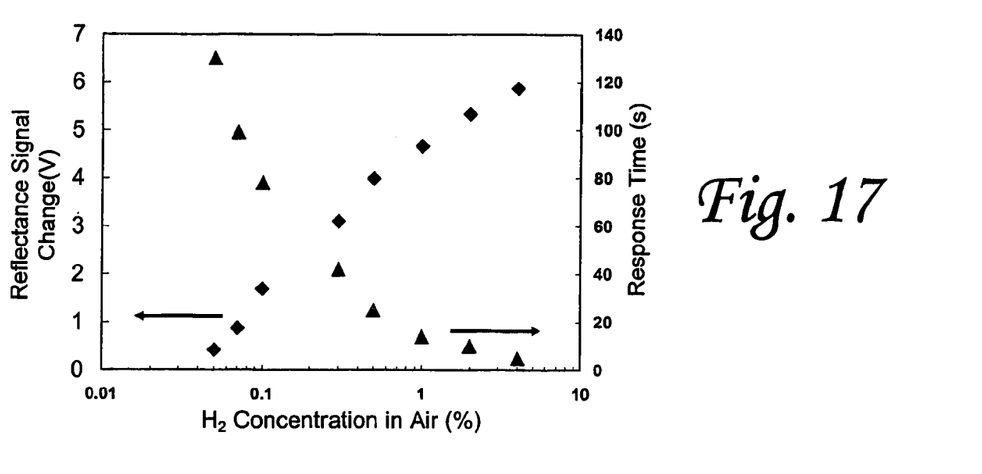
FIG. 17 is a graph of the reflectance signal change and response time as a function of hydrogen gas concentrations ranging from 0.05% to 4% in air for the annealed palladium alloy thin film of FIG. 16.

The sensing characteristic of the $Pd_{0.6}Au_{0.4}$ alloy thin film at an operating temperature of 25° C. was obtained for hydrogen concentrations ranging from 0.05% (500 ppm) to 4%. The signal change and response time as a function of hydrogen concentration are shown in FIG. 17. The signal change is found to be linearly dependent on ln(H2), in contrast to the non-linear dependence displayed by thin films that undergo an α to β PdH phase transition, as commonly reported in the literature for pure Pd or Pd alloys with low metal (e.g. Ag, Ni) contents. Either pure or low alloy content Pd films often suffer from slow response times at these hydrogen levels due to the critical phase response dynamics of the film undergoing the α to β phase transition (the response time can be as long as 3,600 seconds). The linear dependence observed here is typical of a one-phase pressure-composition isotherm, resulting from the addition of a large amount of Au(40 at. %) to Pd.

As shown in FIG. 17, the hydrogen sensitivity of the film has been determined to be 500 ppm within a balance of air. The response time curve in FIG. 17 displays a negative power-law dependence on hydrogen concentration and ranges from 130 seconds to 5 seconds at 0.05% and 4% hydrogen concentrations in air, respectively. A negative power law dependence of the response time with $H_2$ is typical for palladium or palladium alloy thin films not limited by the diffusion of H atoms into the palladium lattice. As described above, these thin films are uninhibited by critical slowing down dynamics, however they are limited by surface interactions. In the present case, these surface limitations are due to the palladium surface covered with pre-adsorbed background gases in an ambient environment that may include water, carbon monoxide and hydrocarbons.

Grain Size

Figure 18:
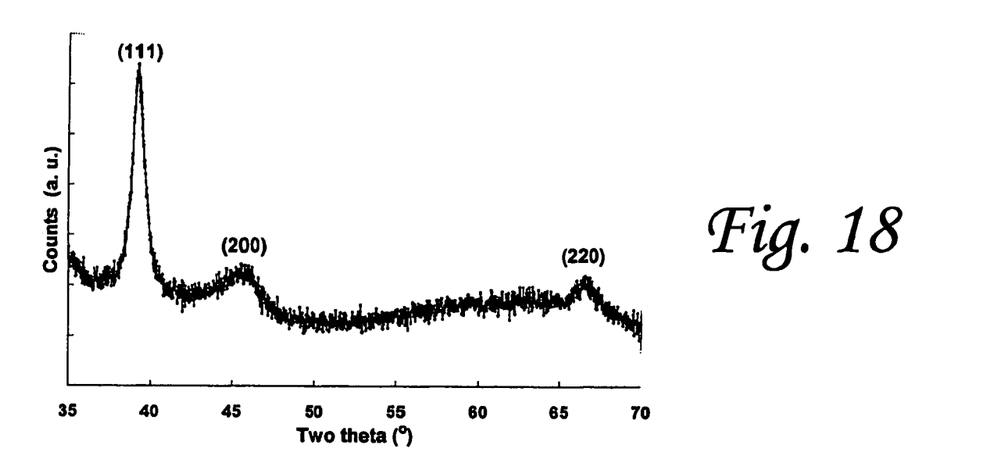
FIG. 18 is an XRD spectrum of the annealed palladium alloy thin film of FIG. 16.

The microstructure of the post-deposition annealed palladium alloy thin films were examined by x-ray diffraction (XRD). The x-ray diffraction patterns were derived on a Scintag XDS 2000 x-ray diffractometer using $CuK_\alpha$ radiation. The XRD system was equipped with a horizontal wide angle four axis goniometer with stepping motors, which allow independent or coupled θ/2θ axes motion. XRD spectra were collected in the standard θ-2θ mode with 2θ ranging from 25° to 55° in steps of 0.02°. The collected XRD patterns were compared to the Au and Pd reference patterns from the standard Joint Committee for Powder Diffraction Standards (JCPDS) powder diffraction files: PDF# 050681 for Pd and PDF# 040784 for Au. The average crystallite grain size D was calculated from the Scherrer formula, $D=0.941\lambda/B \cos(\theta)$ where λ is the x-ray wavelength, B is the FWHM of the appropriate XRD peak and θ is the diffraction angle. A typical XRD spectrum is displayed in FIG. 18 for a 20 nanometer thick film annealed at 200° C. for one hour in an argon atmosphere. The (111), (200) and (220) peaks are clearly distinguished and represent peak positions for a 60:40 PdAu solid solution. About an 8 nanometer average grain size was calculated from the FWHM of the (111) peak using the Scherer formula. A strong dependence of the Pd alloy hydrogen absorption and response time on the resulting grain size, internal stress and crystalline composition as discussed above.

Temperature Dependence

To further explore the dependence of the surface limiting step and to characterize the operating specifications of this palladium alloy material, the thin film was tested as a function of the operational temperature at several hydrogen concentrations.

Figure 19:
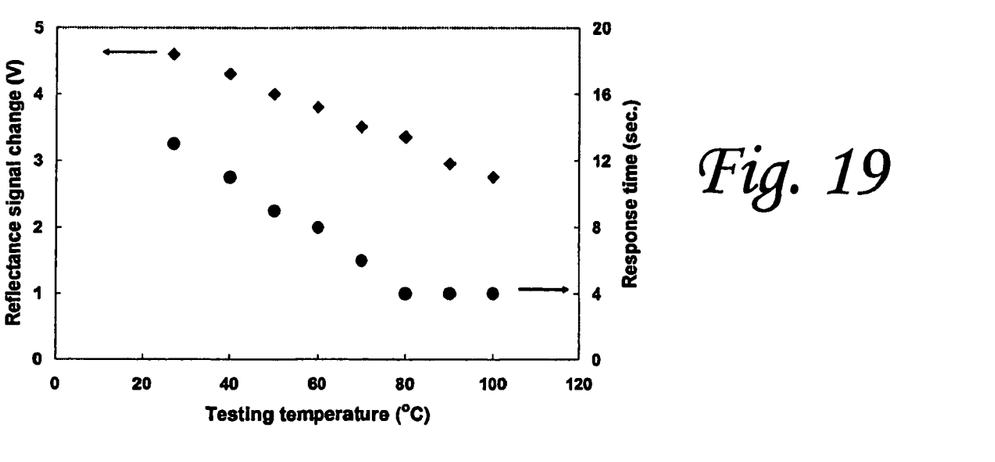
FIG. 19 is a graph of the reflectance signal change and response time as a function of testing temperature for 1% hydrogen gas in air for the annealed palladium alloy thin film of FIG. 16.

FIG. 19 illustrates the signal change and response time vs. temperatures ranging from ambient to 100° C. for 1% hydrogen in air. The signal change decreased linearly with increasing temperature, resulting in an overall 40% reduction in signal change at 100° C. as compared to room temperature operation. This signal reduction is due to the decrease in solubility of hydrogen in the palladium alloy film at elevated temperatures.

The response time also decreased linearly from 12 seconds at 30° C. to 4 seconds at temperatures of 80° C. and above. The saturated response time is believed to arise from dead volume factors of the experimental bench, which have a nominal purge time of the same magnitude.

Relative Humidity Dependence

Since a change in relative humidity affects the palladium alloy surface characteristics due to adsorbed water, the $Pd_{0.6}Au_{0.4}$ thin film was tested as a function of both the operating temperature and relative humidity. A NAFION-based water permeable membrane was utilized for humidification of the room temperature air and hydrogen-air mixtures. Humidity levels were controlled by varying the flow rate through the permeable membrane and were measured at the exit of the testing chamber using an Omega RH411 humidity probe.

Figure 20:
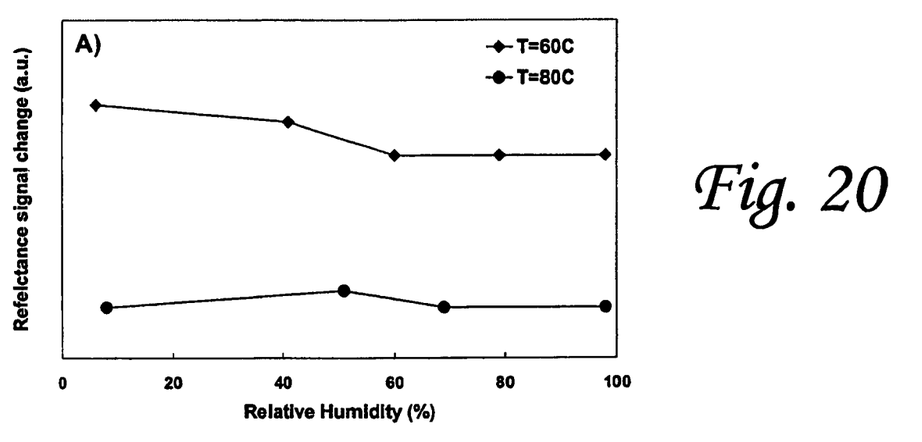
FIG. 20 is a graph of the reflectance signal change as a function of humidity for 1% hydrogen gas in air exposure for the annealed palladium alloy thin film of FIG. 16.
Figure 21:
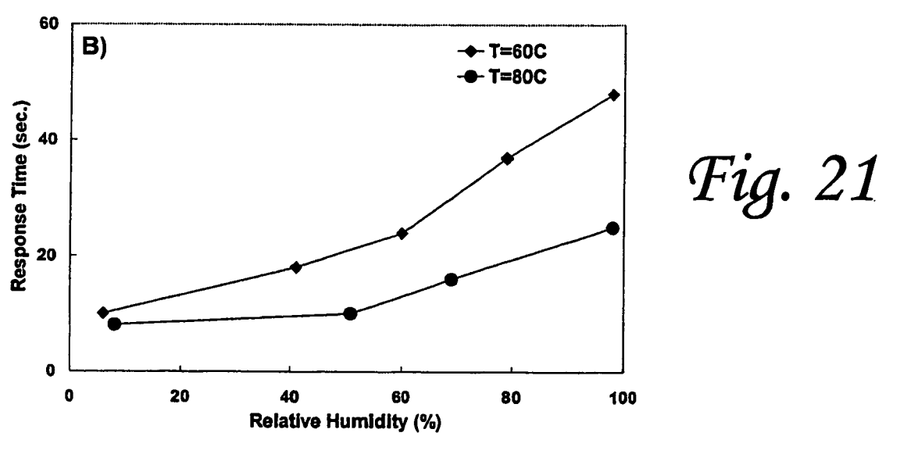
FIG. 21 is a graph of the response time as a function of humidity for 1% hydrogen gas in air exposure for the annealed palladium alloy thin film of FIG. 16.

FIGS. 20 and 21 illustrate the signal change and response time, respectively, of the thin film exposed to 1% hydrogen in air with the humidity ranging from 5% to 95%. Air or hydrogen-air mixtures at ambient temperature (25° C.) were originally humidified to levels ranging from 5% RH (relative humidity) to 95% RH before being delivered to the test cell operating at 60° C. or 80° C. The signal change at both 60° C. and 80° C. displays little dependence on humidity, however as shown in FIG. 21, the response time at both operating temperatures have a strong dependence on RH. At 60° C., the response time increased by a factor of 5, while at 80° C. the response time only increased by a factor of 2.5. The response time increase is due to water adsorption on the film surface which consequently decreases the number of active sites available for the dissociative chemisorption of hydrogen and likewise increases the response time of the palladium alloy thin film. The results indicate that at an elevated operating temperature, an increase in RH has less influence on the sensor response time due to a reduction in the amount of adsorbed water on the Pd alloy surface and the faster reaction kinetics at elevated operating temperatures.

CO and $CO_2$ Dependence

Figure 22:
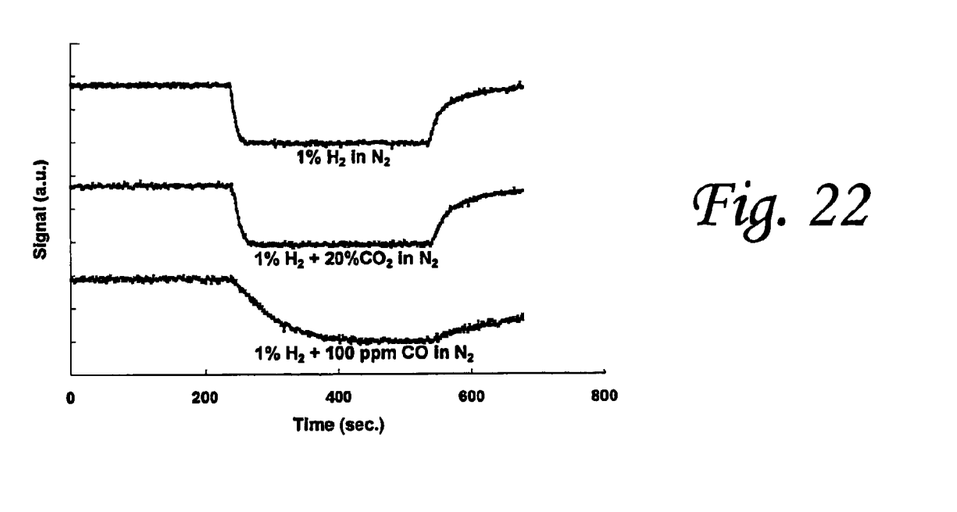
FIGS. 22 and 23 are graphs of the reflectance signal as a function of time upon exposure to various concentrations of gases for the annealed palladium alloy thin film of FIG. 16.

Cross sensitivity measurements were also performed against levels of background CO and $CO_2$. FIG. 22 compares the sensor responses from pure nitrogen to three chemical gas mixtures with nitrogen: 1% H2, 1% $H_2$ and 100 ppm CO, and 1% $H_2$ and 20% $CO_2$ at an operating temperature of 25° C.

As observed in FIG. 22, there is no obvious influence of the added $CO_2$ on the sensor response to the 1% hydrogen mixture. However, upon addition of 100 ppm of CO into the 1%

$H_2/N_2$ mixture there is an increase in response time from about 18 seconds to about 150 seconds with no measurable difference on the signal change at this CO concentration. Similar to the effects of relative humidity, this increase in response time is the result of CO binding to active Pd sites, thus increasing the time required for $H_2$ dissociative chemisorption.

Figure 23:
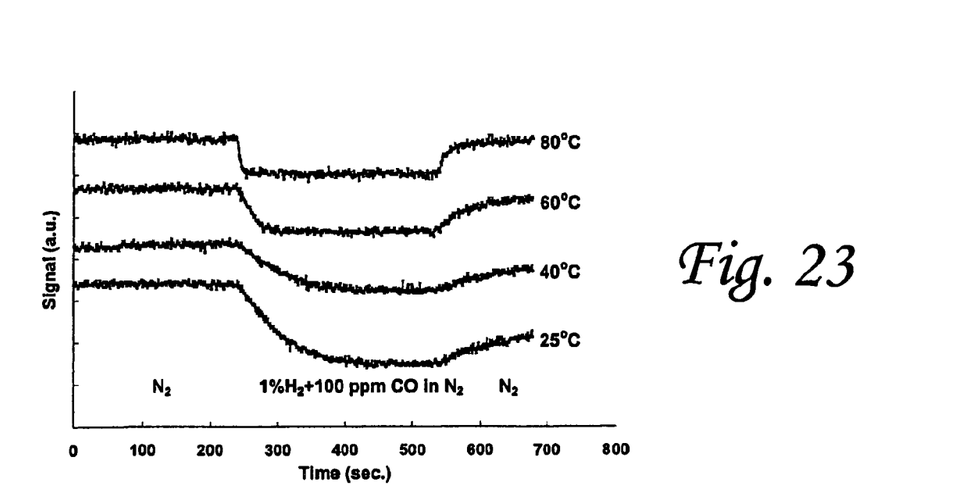

The CO exposure experiments were followed by tests at increased operating temperatures while exposing the film to 1% $H_2$ mixed with 100 ppm CO in nitrogen. FIG. 23 illustrates the results of this test with the sensor operating temperature increasing from 25° C. to 80° C. The response time decreases from 150 seconds at 25° C. to 8 seconds at 80° C., marking a strong reduction of the surface bound CO species. The decrease in the signal change with an increase in temperature is again due to decreased hydrogen solubility. Thus, with the presence of 100 ppm of background CO, an elevated operating temperature is required to maintain a seconds level response time.

Reliability Testing

A series of hydrogen exposure experiments were performed to determine the reliability of the palladium alloy thin films. The reliability tests were formulated around two sets of tests on a palladium alloy thin film: 1) twenty three tests of 4% hydrogen in a balance of air were performed over a one month time frame at ambient temperatures, and 2) the film was tested one month later and then again 10 months later against a 2% hydrogen in air mixture.

Figure 24:
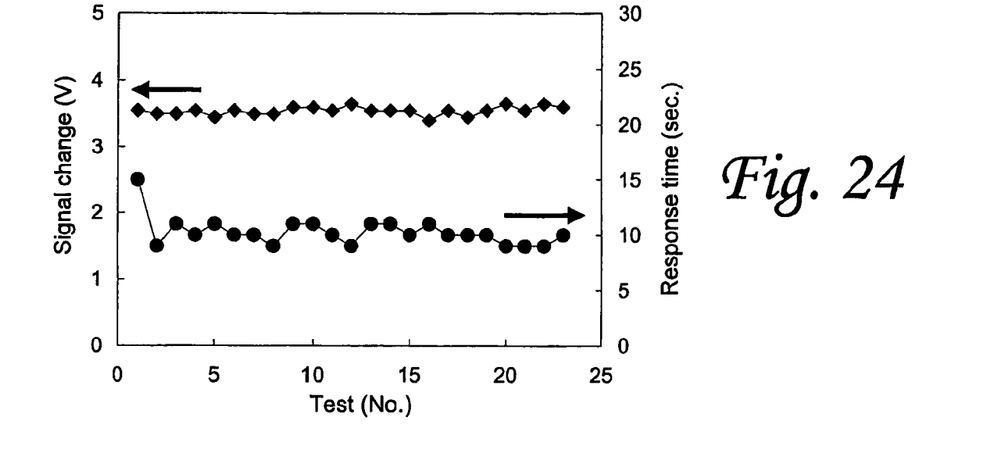
FIG. 24 is a graph of the signal change and response time as a function of test number of reliability measurements over a one month time period involving 23 separate gas exposure tests wherein each test consisted of a 4% hydrogen in a balance of air mixture at 25° C.

As observed in FIG. 24, the signal change and response time vary by 2% and 13% respectively over the one month time frame. While the signal change has an acceptable level of variance, the response times are clearly not a reliable sensing parameter.

Figure 25:
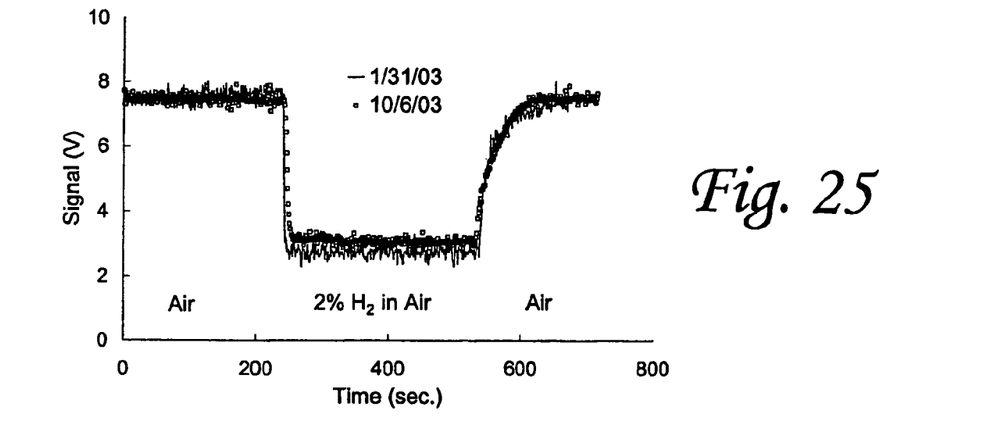
FIG. 25 is a graph of the reflectance signal as a function of time for the reliability measurement of a single film of FIG. 24.

Our previous studies have determined that the initial uptake rate of hydrogen into these palladium thin films is limited not by diffusion into the thin films, but by the adsorbed surface impurities that prevent the dissociative chemisorption process from proceeding with unit probability. Therefore, the increased variability in the response time can be attributed to subtle changes in the adsorbed gas composition which was not controlled in the experimental process. FIG. 25 displays the results of the 8 month long stability study and it was determined that both the signal change and response times are within the variability seen in the month long intensive study.

Conclusion Regarding the Second Samples

The sensitivity of these thin films is 500 ppm with a room temperature response time of 130 seconds at this lower limit of detection, while the 4% $H_2$ in air measurement had a room temperature response time of about 5 seconds. Both the signal and response times linearly decreased with an increase in temperature from ambient levels up to 80° C. due to a decrease in the solubility of hydrogen and an increase in the PdH formation rate respectively. Response times towards 1% hydrogen in ambient air had a response time of 4 seconds at an 80° C. operating temperature which is comparable to industrially available electrically based hydrogen sensors. Hydrogen exposure experiments were performed in the presence of water, CO and $CO_2$ background gases. With water or 100 ppm CO as the background gas, the ultimate signal change was unaffected, while the response time was slowed due to the surface adsorption of water or CO, thereby preventing the immediate dissociative chemisorption of the hydrogen target gas. A subsequent increase in the operating temperature in the presence of hydrogen and the background gases decreased the quantity of surface adsorbed background gases and increased the reaction kinetics, and the response time decreased accordingly. A large background of 20% $CO_2$ had no affect on the hydrogen sensing properties of this film. Reliability tests over both a one month intensive study and experiments performed over a 8 month time frame have shown the high content alloy film to have a 2% and 13% variability in signal change and response time, respectively.

The all-optical sensing specifications that have been detailed are comparable to electrically based sensors and therefore, serve as a promising alternative for electrical-based sensors which are not suitable for sensing applications that are remote in nature, have large electromagnetic interferences, or have large background hydrocarbon impurities.

From the present description it will be appreciated that palladium-gold alloys with a gold content greater than 17 at. % will produce films that will not be inhibited by the PdH α to β phase transition induced critical slowing down phenomena. From extension of this invention, these palladium alloy films would require a thermal annealing process to relieve residual stress while maintaining a grain size of about the same as a grain size of the nonannealed palladium alloy thin film via selection of an appropriate annealing temperature. From the present description it will be appreciated that other metals may be employed in the palladium alloy thin film. For example, the palladium alloy thin film may comprise appropriate amounts of metals such as silver, nickel, copper, and other species known in the art. While a 20 nanometer thin film has been described above, it will be appreciated that the thin film may have a thickness between about 5 nanometers and about 40 nanometers.

Although preferred embodiments have been depicted and described in detail herein, it will be apparent to those skilled in the relevant art that various modifications, additions, substitutions and the like can be made without departing from the spirit of the invention and these are, therefore, considered to be within the scope of the invention as defined in the following claims.

The invention claimed is:

1. A method for forming a hydrogen sensing material, the method comprising:
    forming a palladium-gold alloy thin film comprising about 60 atomic percent of palladium and about 40 atomic percent of gold, said palladium-gold alloy thin film having a thickness between about 5 nanometers and about 40 nanometers; and
    annealing the palladium-gold alloy thin film at a temperature of about 200 degrees Celsius to about 300 degrees Celsius so that the annealed palladium-gold alloy thin film comprises crystalline grains having a nanocrystalline grain size of less than about 10 nanometers.

2. The method of claim 1 wherein the annealing of the palladium-gold alloy thin film comprises maintaining the palladium-gold alloy thin film at the temperature of about 200 degrees Celsius for about 1 hour.

3. The method of claim 1 wherein the annealing results in the nanocrystalline grain size of the annealed palladium-gold alloy thin film of about 8 nanometers.

4. The method of claim 1 further comprising curing the annealed palladium-gold alloy thin film by exposing the annealed palladium-gold alloy thin film to two consecutive cycles of 4-percent hydrogen exposure for about 10 minutes and exposing the annealed palladium-gold alloy thin film to pure nitrogen for about 20 minutes.

5. The method of claim 1 wherein the forming comprises sputtering the palladium and gold.

6. The method of claim 1 wherein the forming the palladium-gold alloy thin film comprises forming the palladium-gold alloy thin film having a thickness about 20 nanometers.

7. A method for detecting hydrogen containing gas, the method comprising:
   providing a hydrogen sensing material formed by the method of claim 1;
   projecting light onto the hydrogen sensing material;
   exposing the hydrogen sensing material to the hydrogen containing gas;
   maintaining the hydrogen sensing material in a single phase when exposing the hydrogen sensing material to the hydrogen containing gas; and
   observing a change in at least one of light transmitted through and reflected from the hydrogen sensing material due to the exposure to the hydrogen containing gas.

8. An optical hydrogen sensor comprising:
   a hydrogen sensing material formed by the method of claim 1;
   a light source for projecting light onto said hydrogen sensing material; and
   a light detector for detecting at least one of light transmitted through and reflected from said hydrogen sensing material.

9. A hydrogen sensing material comprising:
   a palladium-gold alloy thin film comprising about 60 atomic percent of palladium and about 40 atomic percent of gold, said palladium-gold alloy thin film having a thickness between about 5 nanometers and about 40 nanometers; and
   wherein the palladium-gold alloy thin film is annealed at a temperature of about 200 degrees Celsius to about 300 degrees Celsius resulting in the thin film being generally stress free with a generally homogeneous nanocrystalline material composition and comprising crystalline grains having a nanocrystalline grain size of less than about 10 nanometers.

10. The hydrogen sensing material of claim 9 wherein the nanocrystalline grain size of the annealed palladium-gold alloy thin film comprises about 8 nanometers.

11. A method for detecting hydrogen containing gas, the method comprising:
    providing a hydrogen sensing material of claim 9;
    projecting light onto the hydrogen sensing material;
    exposing the hydrogen sensing material to the hydrogen containing gas;
    maintaining the hydrogen sensing material in a single phase when exposing the hydrogen sensing material to the hydrogen containing gas; and
    observing a change in at least one of light transmitted through and reflected from the hydrogen sensing material due to exposure to the hydrogen containing gas.

12. An optical hydrogen sensor comprising:
    a hydrogen sensing material of claim 9;
    a light source for projecting light onto said hydrogen sensing material; and
    a light detector for detecting at least one of light transmitted through and reflected from said hydrogen sensing material.

* * * * *